United States Patent [19]

Oesterlin et al.

[11] 4,246,420

[45] Jan. 20, 1981

[54] PROCESS FOR PREPARING 3-(4-PYRIDINYL)-2-CYCLOHENE-1-OXIME

[75] Inventors: Rudolf Oesterlin, East Greenbush; Peter A. Pareene, Sand Lake, both of N.Y.

[73] Assignee: Sterling Drug Inc., New York, N.Y.

[21] Appl. No.: 105,020

[22] Filed: Dec. 19, 1979

[51] Int. Cl.³ .......................................... C07D 213/53
[52] U.S. Cl. .................................... 546/338; 546/156
[58] Field of Search ........................................ 546/338

[56] References Cited

U.S. PATENT DOCUMENTS

| | | | |
|---|---|---|---|
| 4,026,900 | 5/1977 | Gelotte et al. | 546/338 |
| 4,075,217 | 2/1978 | Gelotte et al. | 546/338 |
| 4,111,946 | 9/1978 | Gelotte et al. | 546/340 |

*Primary Examiner*—Alan L. Rotman
*Assistant Examiner*—Robert T. Bond

*Attorney, Agent, or Firm*—R. K. Bair; B. W. Wyatt

[57] ABSTRACT

An improved method of preparing 3-(4-pyridinyl)-2-cyclohexen-1-one oxime from ethyl 5-oxo-2-[(4-pyridinyl)-carbonyl]hexanoate is a one pot sequence which comprises first heating ethyl 5-oxo-2-[(4-pyridinyl)carbonyl]hexanoate with excess sulfuric acid, neutralizing the excess acid, extracting the resulting 3-(4-pyridinyl)-2-cyclohexen-1-one with isopropyl alcohol, draining off the heavier aqueous layer, adding hydroxylamine hydrochloride to the isopropyl alcohol solution of said 2-cyclohexen-1-one, stirring the mixture at reflux, basifying the mixture and evaporating it to dryness, and isolating 3-(4-pyridinyl)-2-cyclohexen-1-one oxime from the residue. The oxime is an intermediate for preparing 3-(4-pyridinyl)aniline, in turn, an intermediate for preparing rosoxacin, an antibacterial agent.

4 Claims, No Drawings

PROCESS FOR PREPARING 3-(4-PYRIDINYL)-2-CYCLOHENE-1-OXIME

BACKGROUND OF THE INVENTION (a) Field of the Invention

This invention relates to an improved process for preparing 3-(4-pyridinyl)-2-cyclohexen-1-oxime, a rosoxacin intermediate, from ethyl 5-oxo-2-[(4-pyridinyl)carbonyl]hexanoate.

(b) Description of the Prior Art

Gelotte et al. U.S. Pat. No. 4,111,946, issued Sept. 5, 1978, shows two sequences for converting ethyl 5-oxo-2-[(4-pyridinyl)carbonyl]hexanoate to 3-(4-pyridinyl)-2-cyclohexen-1-one: (1) heating ethyl 5-oxo-2-[(4-pyridinyl)-carbonyl]hexanoate under aqueous acidic conditions thereby hydrolyzing and decarboxylating it to produce 1-(4-pyridinyl)-hexan-1,5-dione and then reacting said hexan-1,5-dione with a basic condensing agent to produce 3-(4-pyridinyl)-2-cyclohexen-1-one; and, (2) reacting ethyl 5-oxo-2-[(4-pyridinyl)-carbonyl]-hexanoate with a basic condensing agent to produce ethyl 3-(4-pyridinyl)-2-cyclohexen-1one-4-carboxylate and then heating said 4-carboxylate under aqueous acidic conditions to hydrolyze and decarboxylate it to produce 3-(4-pyridinyl)-2-cyclohexen-1-one. The 3-(4-pyridinyl)-2-cyclohexen-1one was then reacted with hydroxylamine to convert it into its oxime, an intermediate for preparing 3-(4-pyridinyl)aniline, in turn, an intermediate for preparing rosoxacin, an antibacterial agent, namely 1-ethyl-1,4-dihydro-4-oxo-7-(4-pyridinyl)-3-quinolinecarboxylic acid.

SUMMARY OF THE INVENTION

The invention relates to an improvement in the process for converting ethyl 5-oxo-2-[(4-pyridinyl)carbonyl]-hexanoate to 3-(4-pyridinyl)-2-cyclohexen-1-one and, in turn, converting the cyclohexen-1-one to its oxime, the improvement which comprises using a one pot sequence of first heating ethyl 5-oxo-2-[(4-pyridinyl)carbonyl]hexanoate with excess aqueous sulfuric acid, neutralizing the excess acid, extracting the resulting 3-(4-pyridinyl)-2-cyclohexen-1-one with isopropyl alcohol, draining off the heavier aqueous layer, adding hydroxylamine hydrochloride to the isopropyl alcohol solution of 3-(4-pyridinyl)-2-cyclohexen-1-one, stirring the mixture at reflux, basifying the mixture and evaporating it to dryness, and isolating the 3-(4-pyridinyl)-2-cyclohexen-1-one oxime from the residue.

DETAILED DESCRIPTION INCLUSIVE OF PREFERRED EMBODIMENTS

This invention resides in an improvement in the process for preparing 3-(4-pyridinyl)-2-cyclohexen-1-oxime by heating ethyl 5-oxo-2-[(4-pyridinyl)carbonyl]-hexanoate under aqueous acidic conditions to produce 1-(4-pyridinyl)-hexan-1,5-dione, reacting said hexan-1,5-dione with a basic condensing agent to produce said 3-(4-pyridinyl)-2-cyclohexen-1-one, and converting said cyclohexen-1-one to its oxime, said improvement being a one pot sequence consisting of first heating ethyl 5-oxo-2-[(4-pyridinyl)carbonyl]hexanoate with excess aqueous sulfuric acid, neutralizing the excess acid, shaking the resulting mixture well with isopropyl alcohol to extract the 3-(4-pyridinyl)-2-cyclohexen-1-one, draining off the heavier warm (40° to 50° C.) aqueous layer, adding hydroxylamine hydrochloride to the isopropyl alcohol solution of 3-(4-pyridinyl)-2-cyclohexen-1-one, stirring the mixture at reflux, basifying the mixture and evaporating it to dryness, and isolating the 3-(4-pyridinyl)-2-cyclohexen-1-one oxime from the residue.

In a preferred embodiment three mole-equivalents of sulfuric acid were used per mole of ethyl 5-oxo-2-[(4-pyridinyl)carbonyl]hexanoate, the excess sulfuric acid was neutralized with aqueous sodium hydroxide solution and the reaction mixture was basified after oxime formation with concentrated ammonium hydroxide.

Although three mole-equivalents of sulfuric acid per mole of ethyl 5-oxo-2-[(4-pyridinyl)carbonyl]hexanoate were preferred, from two to four mole-equivalents can be used; however, lower yields are obtained using less than three mole-equivalents and using more than three mole-equivalents is unnecessary. Basification with ammonium hydroxide after oxime formation preferably brought the pH between 7 and 8. The oxime was conveniently and preferably isolated from inorganic salts, mostly ammonium chloride, using aqueous-alkanol, preferably heating the residue with water at about 60° to 80° C. and then adding ethanol.

The improved process of the invention has a number of advantages over the previous Gelotte et al. process, namely: (1) provides a simplified one pot sequence rather than several separate steps; (2) omits the separate steps of heating ethyl 5-oxo-2-[(4-pyridinyl)carbonyl]-hexanoate under aqueous acidic conditions to produce 1-(4-pyridinyl)-hexan-1,5-dione and heating the 1,5-dione with a basic condensing agent to produce 3-(4-pyridinyl)-2-cyclohexen-1-one; (3) uses considerably less (one-third) sulfuric acid, e.g., only three mole-equivalents rather than nine per mole of ethyl 5-oxo-2-[(4-pyridinyl)carbonyl]hexanoate used by Gelotte et al., in turn requiring considerably less sodium hydroxide solution and reducing the volume of reaction mixture; (4) uses isopropyl alcohol as extracting solvent for 3-(4-pyridinyl)-2-cyclohexen-1-one, thereby replacing chloroform and affording the convenient draining off of the unwanted heavy aqueous layer; (5) directly converts the 2-cyclohexen-1-one in the isopropyl alcohol extract to its oxime; and, (6) omitting the purification steps of preparing and recrystallizing the methanesulfonate of the oxime. The oxime prepared by the improved process of the invention can be used directly without further purification in its conversion via its O-acetyl derivative to N-acetyl-3-(4-pyridinyl)aniline.

The following example will further illustrate the invention without, however, limiting it thereto.

To a stirred cooled solution of 250 ml. (4.49 moles) of concentrated sulfuric acid in 800 ml. of water was added 390 g. (1.48 moles) of ethyl 5-oxo-2-[(4-pyridinyl)carbonyl]-hexanoate at such a rate to maintain the temperature below 20° C. The reaction vessel was connected via a downward water-cooled condenser and receiver to a gas meter for measurement of carbon dioxide evolution. The slightly cloudy solution was stirred at ambient temperature overnight. After sixteen hours of stirring, 15% of the theoretical amount of carbon dioxide had evolved. [In another run 41% carbon dioxide had evolved when the reaction mixture had been stirred for sixty-five hours.] The now clear, light brown solution was then gradually heated on a steam bath to 92° C. over three hours accompanied by an increasingly vigorous gas evolution:

| Total Heating Period (Hrs.) | Internal Temp. °C. | % CO$_2$ Evolved |
| --- | --- | --- |
| 0 | 25 | 15 |
| 0.5 | 30 | 16 |
| 1 | 49 | 20 |
| 1.5 | 59 | 27 |
| 2 | 68 | 39 |
| 2.5 | 80 | 60 |
| 3 | 92 | 99 |

During an additional forty minutes at 92° C., the gas evolution virtually ceased. The dark reaction mixture was cooled to 40° C. and was basified with about 800 ml. of 35% aqueous sodium hydroxide with occasional cooling keeping the temperature near 40° C. The separated oil was taken up with 660 ml. of isopropyl alcohol and the heavier aqueous layer was separated while still warm (40° to 50° C.) and discarded. The isopropyl alcohol solution containing 3-(4-pyridinyl)-2-cyclohexen-1-one was used in the following oximation step. To the isopropyl alcohol containing said 2-cyclohexen-1-one was added 120 g. (1.72 moles) of hydroxylamine hydrochloride and the mixture was stirred at reflux for two hours. The still warm solution was basified with about 200 ml. of concentrated ammonium hydroxide. The reaction mixture was evaporated to dryness in vacuo to yield a mixture of 3-(4-pyridinyl)-2-cyclohexen-1-one oxime and inorganic salts, predominantly ammonium chloride. The residue was stirred and heated in 680 ml. of water to 70° C. and 340 ml. of absolute ethanol was added. The mixture was allowed to cool slowly to room temperature with stirring and was ice-cooled prior to filtration of the light beige solid. The product was thoroughly washed with water and dried at 60° C. in vacuo to produce 236 g. (84.8%) of 3-(4-pyridinyl)-2-cyclohexen-1-one oxime, m.p. 172°–181° C. Its nmr spectrum showed no impurities.

I claim:

1. An improvement in the process for preparing 3-(4-pyridinyl)-2-cyclohexen-1-one oxime by heating ethyl 5-oxo-2-[(4-pyridinyl)carbonyl]hexanoate under aqueous acidic conditions to produce 1-(4-pyridinyl)-hexan-1,5-dione, heating said hexan-1,5-dione with a basic condensing agent to produce 3-(4-pyridinyl)-2-cyclohexen-1-one, and converting said cyclohexen-1-one to its oxime, said improvement being a one pot sequence consisting of first heating ethyl 5-oxo-2-[(4-pyridinyl)carbonyl]hexanoate with excess aqueous sulfuric acid, neutralizing the excess acid, shaking the resulting warm mixture well with isopropyl alcohol to extract the 3-(4-pyridinyl)-2-cyclohexen-1-one, draining off the heavier warm aqueous layer, adding hydroxylamine hydrochloride to the isopropyl alcohol solution of 3-(4-pyridinyl)-2-cyclohexen-1-one, stirring the mixture at reflux, basifying the mixture and evaporating the reaction mixture to dryness, and isolating the 3-(4-pyridinyl)-2-cyclohexen-1-one oxime from the residue.

2. The process according to claim 1 where three mole-equivalents of sulfuric acid are used per mole of ethyl 5-oxo-2-[(4-pyridinyl)carbonyl]hexanoate.

3. The process according to claim 1 where the excess sulfuric acid was neutralized with aqueous sodium hydroxide solution.

4. The process according to claim 1 where the reaction mixture was basified after oxime formation with concentrated ammonium hydroxide to a pH between 7 and 8.

* * * * *